(12) United States Patent
Pandelisev

(10) Patent No.: US 7,177,696 B1
(45) Date of Patent: Feb. 13, 2007

(54) MULTIPLE SELECTABLE FIELD/CURRENT-VOLTAGE PADS HAVING INDIVIDUALLY POWERED AND CONTROLLED CELLS

(75) Inventor: Kiril A. Pandelisev, Mesa, AZ (US)

(73) Assignee: H & P Medical Research, Inc., Mesa, AZ (US)

( * ) Notice: Subject to any disclaimer, the term of this patent is extended or adjusted under 35 U.S.C. 154(b) by 1270 days.

(21) Appl. No.: 09/587,318

(22) Filed: Jun. 5, 2000

Related U.S. Application Data

(60) Provisional application No. 60/138,300, filed on Jun. 9, 1999.

(51) Int. Cl.
*A61N 1/36* (2006.01)

(52) U.S. Cl. ......................... 607/51; 607/148
(58) Field of Classification Search ............ 607/50–52, 607/148; 600/393, 9–15
See application file for complete search history.

(56) References Cited

U.S. PATENT DOCUMENTS

| | | | |
|---|---|---|---|
| 1,425,743 A | 8/1922 | Baruch | |
| 3,025,857 A * | 3/1962 | Browner | ..................... 607/115 |
| 4,240,437 A | 12/1980 | Church | |
| 4,312,340 A | 1/1982 | Donadelli | |
| 4,381,012 A * | 4/1983 | Russek | ........................ 600/382 |
| 4,390,023 A | 6/1983 | Rise | |
| 4,690,146 A * | 9/1987 | Alon | ........................... 607/66 |
| 4,779,593 A | 10/1988 | Kiernan | |
| 4,895,154 A | 1/1990 | Bartelt et al. | |
| 4,922,906 A | 5/1990 | Takeuchi et al. | |
| 4,926,864 A | 5/1990 | Dufresne et al. | |
| 4,982,742 A | 1/1991 | Claude | |
| 5,038,780 A | 8/1991 | Boetzkes | |
| 5,158,780 A | 10/1992 | Schraven et al. | |
| 5,195,940 A | 3/1993 | Baylink | |
| 5,251,623 A | 10/1993 | Groux et al. | |
| 5,336,247 A | 8/1994 | Groux et al. | |
| 5,344,384 A * | 9/1994 | Ostrow et al. | ................. 600/13 |
| 5,512,057 A | 4/1996 | Reiss et al. | |
| 5,518,496 A * | 5/1996 | McLeod et al. | .............. 607/51 |

\* cited by examiner

*Primary Examiner*—George Evanisko
(74) *Attorney, Agent, or Firm*—Cermak & Kenealy, LLP

(57) ABSTRACT

A method and apparatus for speeding the healing process of soft tissues, bone fractures, cancerous tissue, nerve pathways and other body tissues wherein a portable base comprising a plurality of cells is applied with the cells facing or encircling the wound. The cells generate electro-magnetic radiations, radio frequencies, magnetic fields, current-voltage signals or combinations thereof via a field generator coil or electrodes. Each cell is powered and controlled individually via self-contained controls or remote controls. The type, frequency, pulse characteristics, repetition rate and signal density of the energy are varied according to the size and type of wound to be treated and according to the proximity of each cell to the wounded tissue.

36 Claims, 16 Drawing Sheets

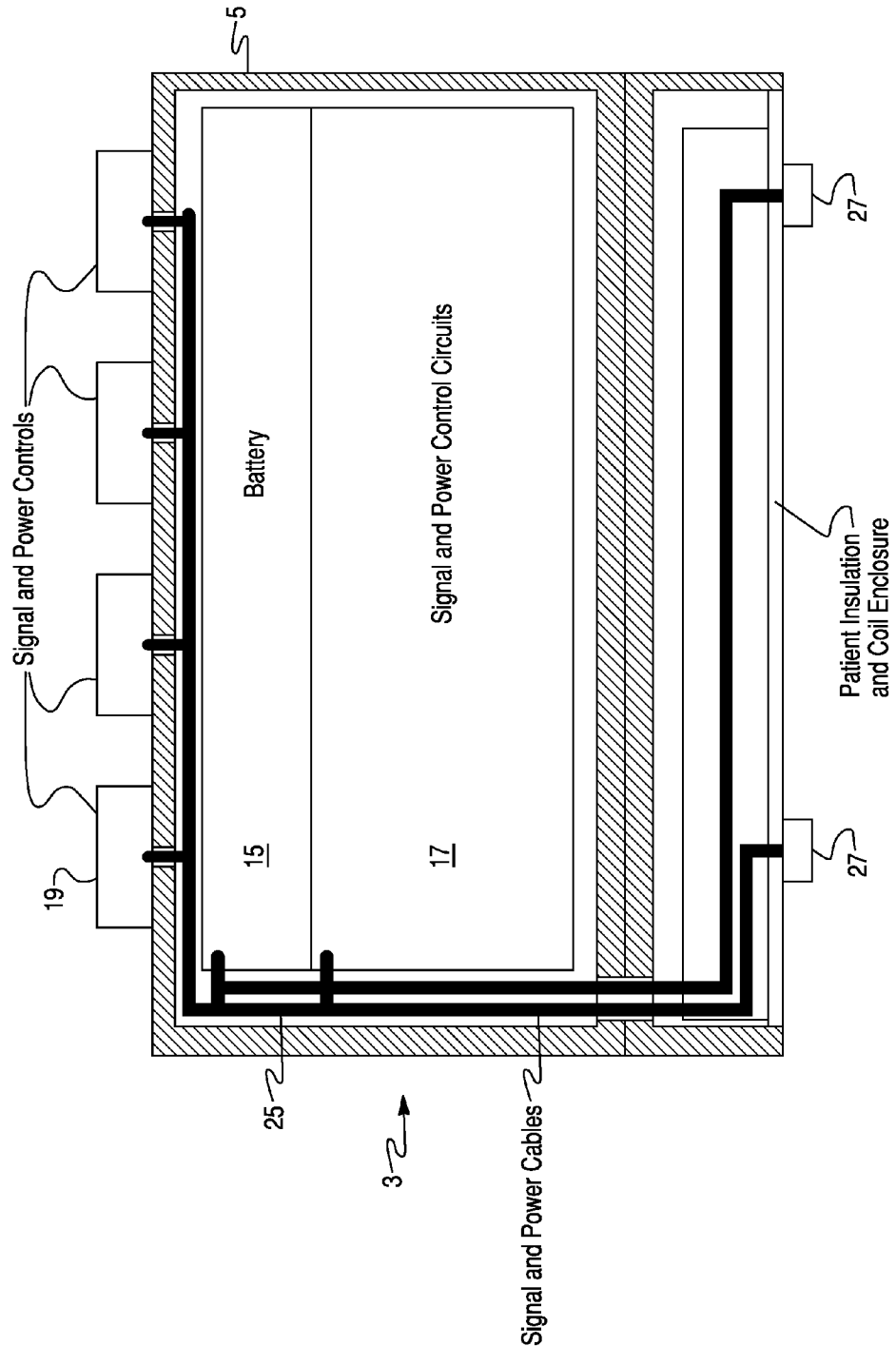

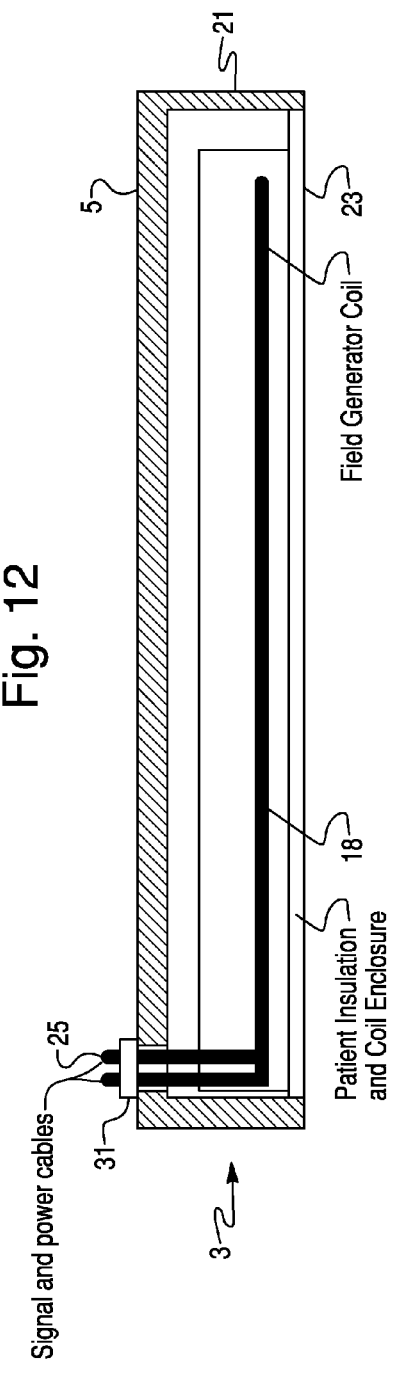
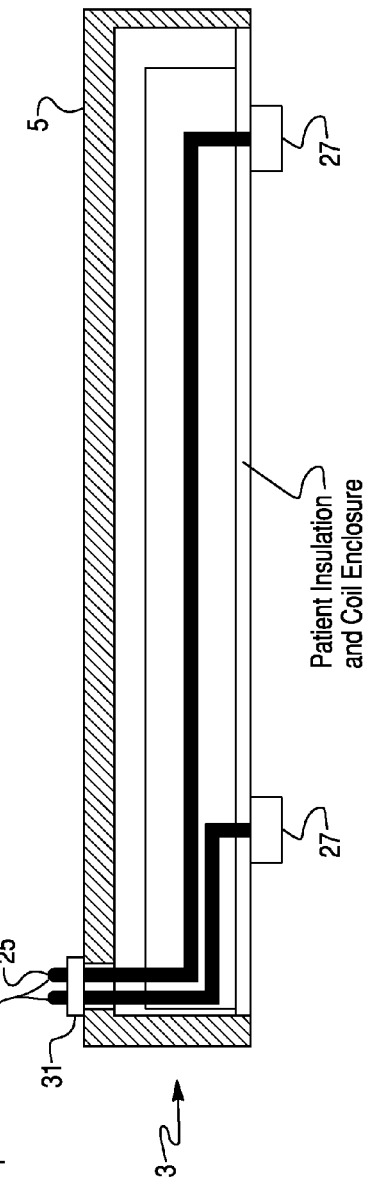

MULTIPLE SELECTABLE FIELD/CURRENT-VOLTAGE PADS HAVING INDIVIDUALLY POWERED AND CONTROLLED CELLS

This application claims the benefit of U.S. Provisional Application No. 60/138,300, filed Jun. 9, 1999.

BACKGROUND OF TUE INVENTION

Several modes of therapeutic treatments of wounds are in vogue. Electro-magnetic radiation devices, electrical tissue stimulators, and massage apparatuses are currently in use for stimulating the body's healing processes. Generally, those treatment methods involve placing electrodes on the body and providing an electrical field to stimulate the body part.

Needs exist for portable devices that can be used anywhere at any time to apply energy to wounded tissue and that are capable of being variably controlled within the body of the device. The present invention meets requirement lacking in prior art devices.

SUMMARY OF THE INVENTION

The present invention is a flexible and fully portable unit employing individually powered and controlled cells that produce a radio frequency (RF), electromagnetic radiation (EM), a magnetic field (B) or a current-voltage signal for healing purposes. The cells may have self-contained controls or be remote controlled. The unit may contain only one type of cell or it may be made up of a combination of radiation and signal producing cells. The cells may be of any shape, any size and may be combinations thereof of variable sizes and shapes.

The type of radiation or current-voltage application used, the strength of the radiation or current-voltage, the pattern of activated cells, the frequency of the signal, the pulse characteristics and its width, the repetition rate, the strength of the signal, the use of a continuous or a pulsating mode, the signal density per unit area, as well as the composition of the cells comprising the pad are determined by the wound being treated, the size and shape of the wound, the depth of the wound, and the type of tissue being treated. The tissue may be soft tissue, a bone fracture, cancerous tissue, a nerve path, or any other body type tissue.

In the case of RF/EM/B applications, certain patterns of the applied field, the pattern of activated cells, the frequency of the signal, the pulse characteristics and the pulse width, the repetition rate, the strength of the signal, the use of a continuous or a pulsating mode, and the signal density per unit area bring very improved healing results over the current techniques.

In the case of current-voltage applications, the choice of applying various signals at selected areas at the periphery of the wound, or across the wound, or any combinations thereof, speeds up the healing process and also provides for applications that are not possible with present techniques.

The combination of a RF/EM/B field and a current-voltage application furthers the non-invasive techniques for healing of various parts of the body.

The unit consists of a pad that fits on a body part, having multiple small radio frequency transmitters arranged in an array. The transmitter coils directly above a wound are energized to transmit pulsed radio frequency energy to the wound periphery or center or both. Transmitters in the array which are not near the wound are deactivated. As a result, energy is focused on the wound periphery and/or central area to promote rapid healing and tissue growth there. The results are physiological activity at the wound site. Low energy can make a device portable, self-contained and reusable on different wounds after sterilization. One size of the pad fits all. The use of the pad allows for the body's healing energy to be focused precisely where needed, speeding healing and tissue growth.

The unit is portable, allowing the user to obtain the benefits of the unit at any time or location. The unit is extremely flexible in the available methods of providing power to the individual cells. Each cell may be supplied power individually by already incorporated power and signal capabilities. Each cell may be supplied power remotely, by either enabling the desired cells via connections to a control package that is located at one or both ends of the pad, by flexible module surrounding the pad, or by a separate control unit that is powered by standard batteries, rechargeable batteries, or simply by connecting the control unit to a power outlet. Each cell may be turned ON or OFF by a switch on the cell or by a control unit.

The pad is thin, flexible and portable. It may be used by applying the pad over the patient with the cell surface facing down, under the patient with the cell surface facing up, or in any other desired position. The flexible nature of the pad allows for shaping of the pad and applying it around a leg, arm or any other part of the body that needs treatment. The number of the activated cells as well as the shape of the area that is subjected to the RF/EM/B field or the current-voltage signals, or a combination thereof, and the signal strength, the frequency and other signal characteristics greatly depends on the shape and size of the wounded area to be treated.

Sensors may be incorporated into the pad allow for measuring the dose of the treatment, the temperature of the treated area, blood pressure, or any other relevant parameters.

The cost of maintenance of the pad and the effectiveness of the pad in treating patients is drastically lowered by simply repairing the defective cells.

The invention is a healing cell apparatus comprising a base on which a plurality of cells is arranged orthogonally for application to wounds on a body. The cells apply energy to the wound and peripheral areas of the body, speeding the healing process of soft tissues, bone fractures, cancerous tissues, nerve pathways and other body tissues. The base may be thin, flexible and portable. A power supply individually communicates independently with each of the plurality of cells, and controls connected to the cells control application of power to each of the cells individually. The cells generate radio frequencies, electro-magnetic radiations, magnetic fields, current-voltage signals, and combinations thereof. The type, strength, pattern, frequency, pulse characteristics, width, repetition rate and signal density of the energy is varied according to the type and size of the wound to be treated and proximity of the cells to the wound. The frequency and field strength of the energy generated by the cells is varied and increases with proximity to a wound. A number of activated cells may be varied. The base may be applied with the cells facing the wound, or encircling a limb. Sensors may be incorporated into the base to measure the dose of the treatment, the temperature of the treated area, blood pressure or other relevant parameters.

The power source may be batteries or a connection to a power outlet, a converter and oscillator, and a transformer. The power source may be mounted on the base, on one end of the base, or on opposite ends of the base. The power source may be connected to the base. Power and signal conduits may be mounted on the base. The power and signal conduits connect to a power and signal generator and control. The power and signal generator and control may be portable.

A control panel, a power supply, and a signal generator and control may each be mounted on either end of the base, or on opposite ends of the base.

Cells may have self-contained controls, which are connected to batteries. Additionally, the cells comprise external connectors on each cell for connecting the cells to external signal and power controls. The self-contained controls for cells which generate electromagnetic radiations, radio frequencies, magnetic fields, and combinations thereof comprise power and signal control circuits connected to the batteries, power and signal cables connected to the signal and power control circuits, a field generator coil for generating energy connected to cables, a shielding separating the control circuits form the coil for shielding the control and any adjacent cells from interference, and a coil enclosure and patient insulation interposed between a patient and the coil. The batteries, controls, shielding, coil and cables are surrounded by a housing.

The self-contained controls for cells which generate current-voltage signals comprise power and signal control circuits, power and signal control cables connected to the power and signal control circuits and to the battery, electrodes connected to the power and signal cables, and patient insulation mounting the electrodes.

Cells may be remotely controlled. The cells which are remotely controlled and generate electromagnetic radiations, radio frequencies, magnetic fields, and combinations thereof. comprise signal and power cables, a field generator coil for generating energy, a coil enclosure, an on/off switch, and shielding for preventing interference with any adjacent cells.

The cells which are remotely controlled and generate current-voltage signals comprise power and signal cables, electrodes, patient insulation, a cable enclosure, and an on/off switch.

These and further and other objects and features of the invention are apparent in the disclosure, which includes the above and ongoing written specification, with the claims and the drawings.

BRIEF DESCRIPTION OF THE DRAWINGS

FIG. 11 is a block diagram of a self-contained current-voltage unit cell.

FIG. 12 is a block diagram of a remote controlled EM/RF/magnet field unit cell.

FIG. 13 is a block diagram of a remote controlled current-voltage unit cell.

DETAILED DESCRIPTION OF THE PREFERRED EMBODIMENTS

Figure 1:
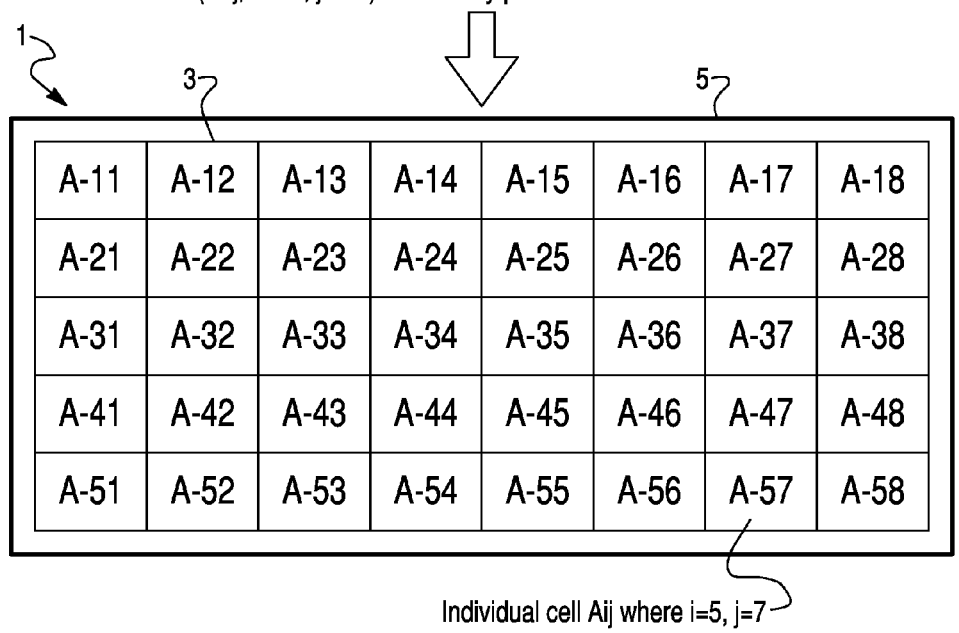
FIG. 1 is a diagram of a multiple selectable field generator having forty individually controlled cells.
Figure 2:
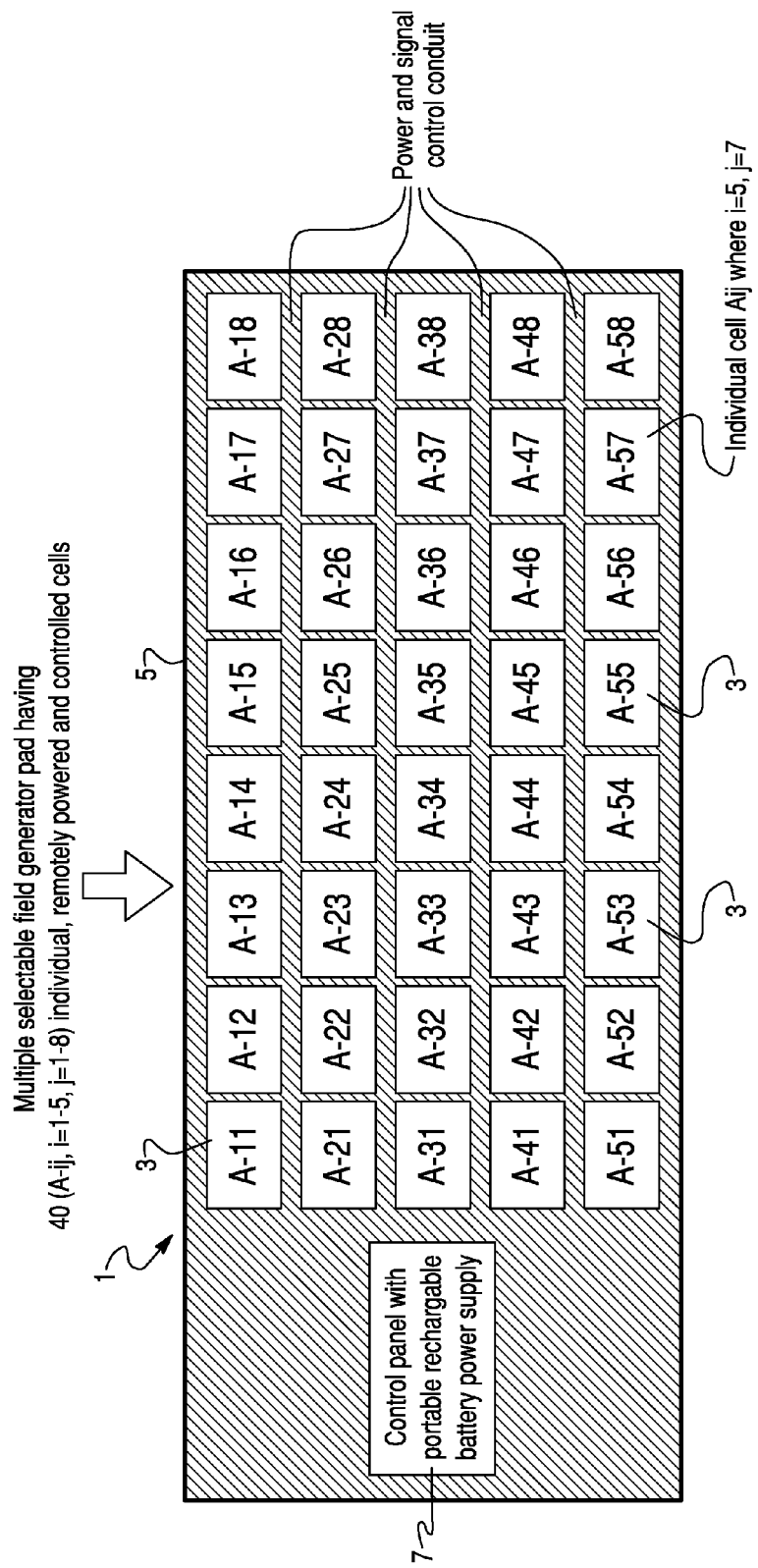
FIG. 2 is a diagram of a multiple selectable field generator having forty individual, remotely powered and controlled cells and a control panel located at only one end of the pad.
Figure 3:
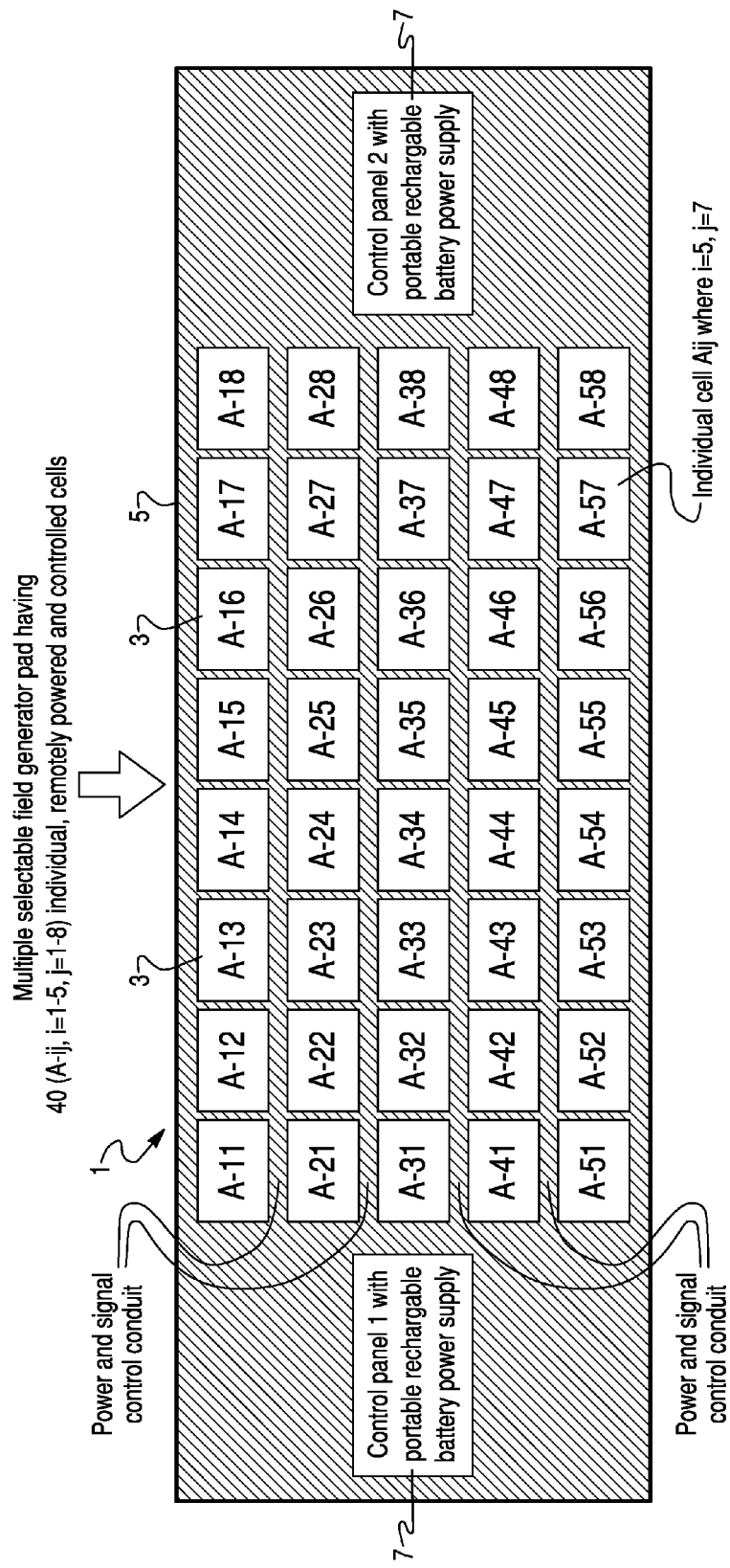
FIG. 3 is a diagram of a multiple selectable field generator having forty individual, remotely powered and controlled cells and a control panel located at both ends of the pad.
Figure 4:
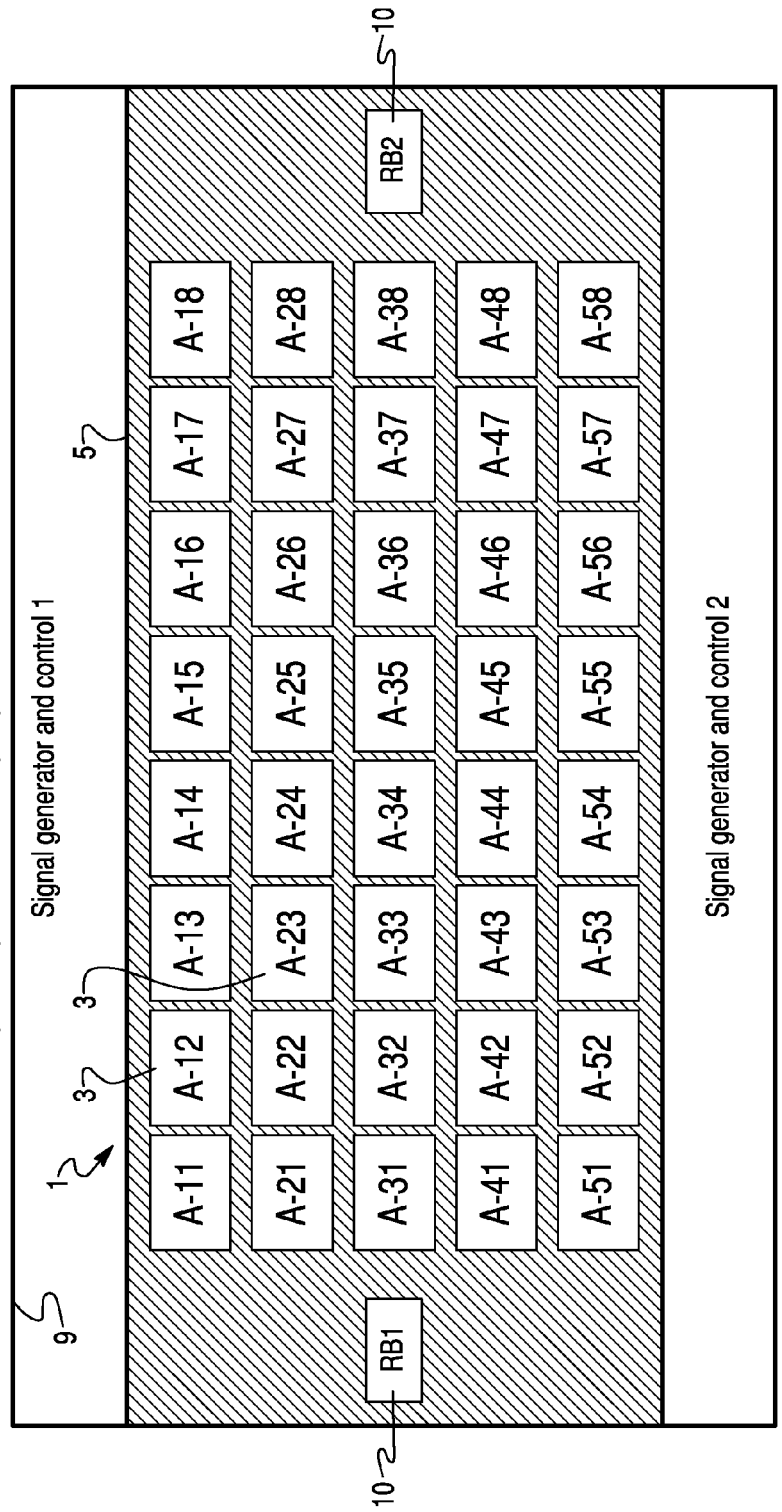
FIG. 4 is a diagram of a multiple selectable field generator pad having forty individual, pad powered and controlled cells that is connected to a portable power signal generator and control.
Figure 5:
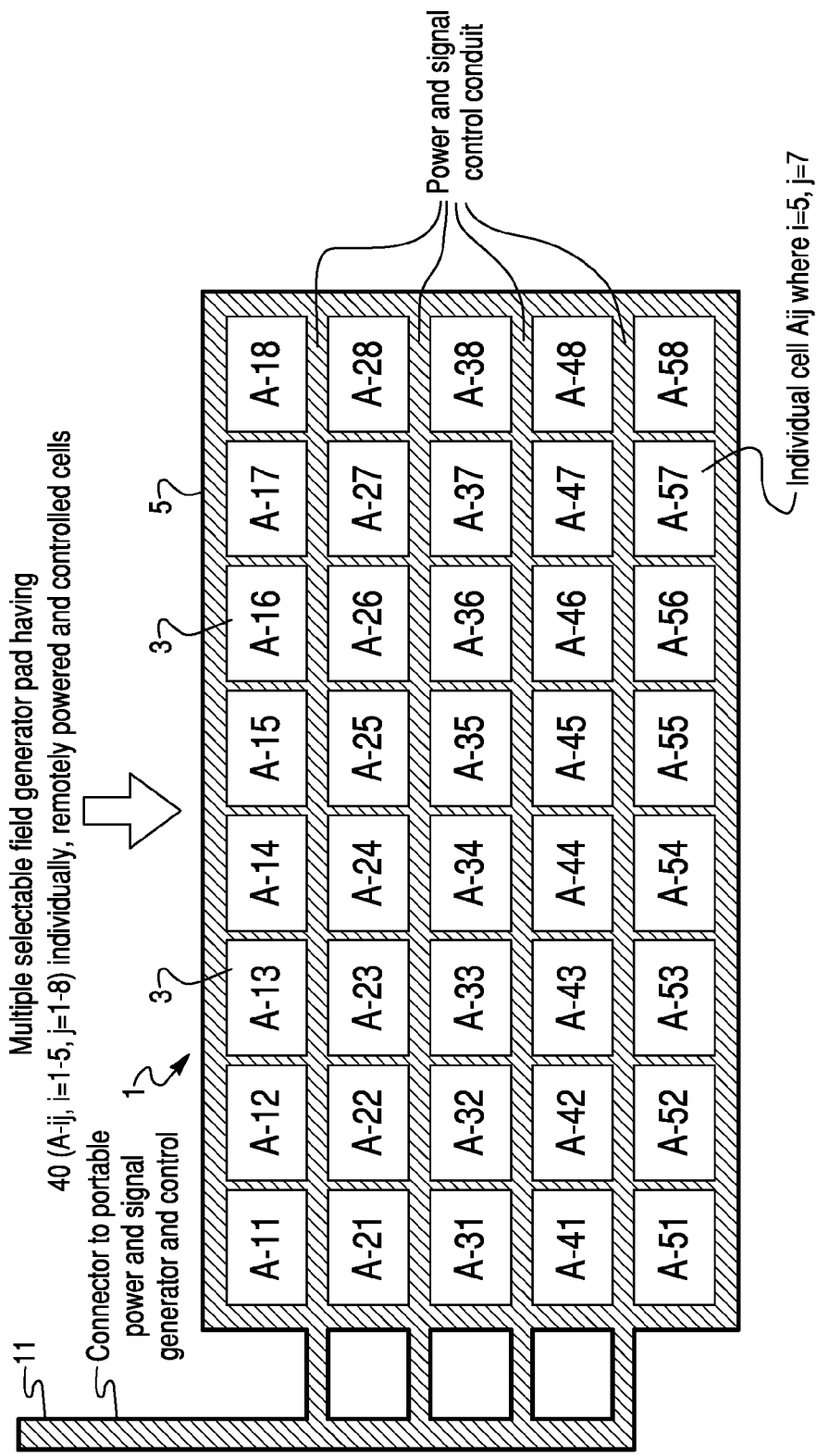
FIG. 5 is a diagram of a multiple selectable field generator pad having forty individual, remotely powered and controlled cells.

The present invention is a flexible and fully portable unit 1 employing individually powered and controlled cells 3 that produce a radio frequency (RF), electromagnetic radiation (EM), a magnetic field (B) or a current-voltage signal for healing purposes, as shown in FIGS. 1–6. The cells 3 are contained in the unit 1 by a pad housing 5. The cells 3 may have self-contained controls, as shown in FIG. 1, or be remotely controlled, as shown in FIGS. 2, 3 and 5. The unit 1 may contain only one type of cell 3 or it may be made up of a combination of radiation and signal producing cells.

The type of radiation or current-voltage application used, the strength of the radiation or current-voltage, the pattern of activated cells, the frequency of the signal, the pulse characteristics and its width, the repetition rate, the strength of the signal, the use of a continuous or a pulsating mode, the signal density per unit area, as well as the composition of the cells 3 comprising the pad 1 are determined by the wound being treated, the size and shape of the wound, the depth of the wound, and the type of tissue being treated. The tissue may be soft tissue, a bone fracture, cancerous tissue, a nerve path, or any other body type tissue.

In the case of RF/EM/B applications, certain patterns of the applied field, the pattern of activated cells, the frequency of the signal, the pulse characteristics and the pulse width, the repetition rate, the strength of the signal, the use of a continuous or a pulsating mode, and the signal density per unit area bring very improved healing results over the current techniques.

In the case of current-voltage applications, the choice of applying various signals at selected areas at the periphery of the wound, or across the wound, or any combinations thereof, speeds up the healing process and also provides for applications that are not possible with present techniques.

The combination of a RF/EM/B field and a current-voltage application furthers the non-invasive techniques for healing of various parts of the body.

The unit 1 is portable, allowing a user to obtain the benefits of the unit at any time or location. The unit 1 is also extremely flexible in the available methods of providing power to the individual cells. Each cell 3 may be supplied power individually by already incorporated power and signal capabilities, as shown in FIG. 1. Each cell 3 may be supplied power remotely, by either enabling the desired cells via connections to a control package 7 that is located at one or both ends of the pad or on a side away from the side facing the user (FIGS. 2 and 3, respectively), by a flexible module surrounding the pad 9 (FIG. 4), or by a separate control unit (FIG. 5) that is connected to the unit by a connector 11 that is powered by standard batteries, rechargeable batteries 10 (FIG. 4), or simply by connecting the control unit to a power outlet. The batteries may be provided between the pad and the power outlet having connections, such as cable or the like, between the batteries, power outlet and the pad. Each cell 3 may be turned ON or OFF by a switch on the cell or by a separate control unit.

The pad 1 is thin, flexible and portable. It may be used by applying the pad over the patient with the cell surface facing down, under the patient with the cell surface facing up, or in any other desired position. The pad may be positioned proximal the body and may be spaced from the body or in contact with the body or be selectively in contact with or spaced from the body depending on the position of individual cells on the pad. For example, the cells may have variable positions on the pad with some of the cells being in contact with the body and some spaced form the body when the pad is in use.

Figure 6:
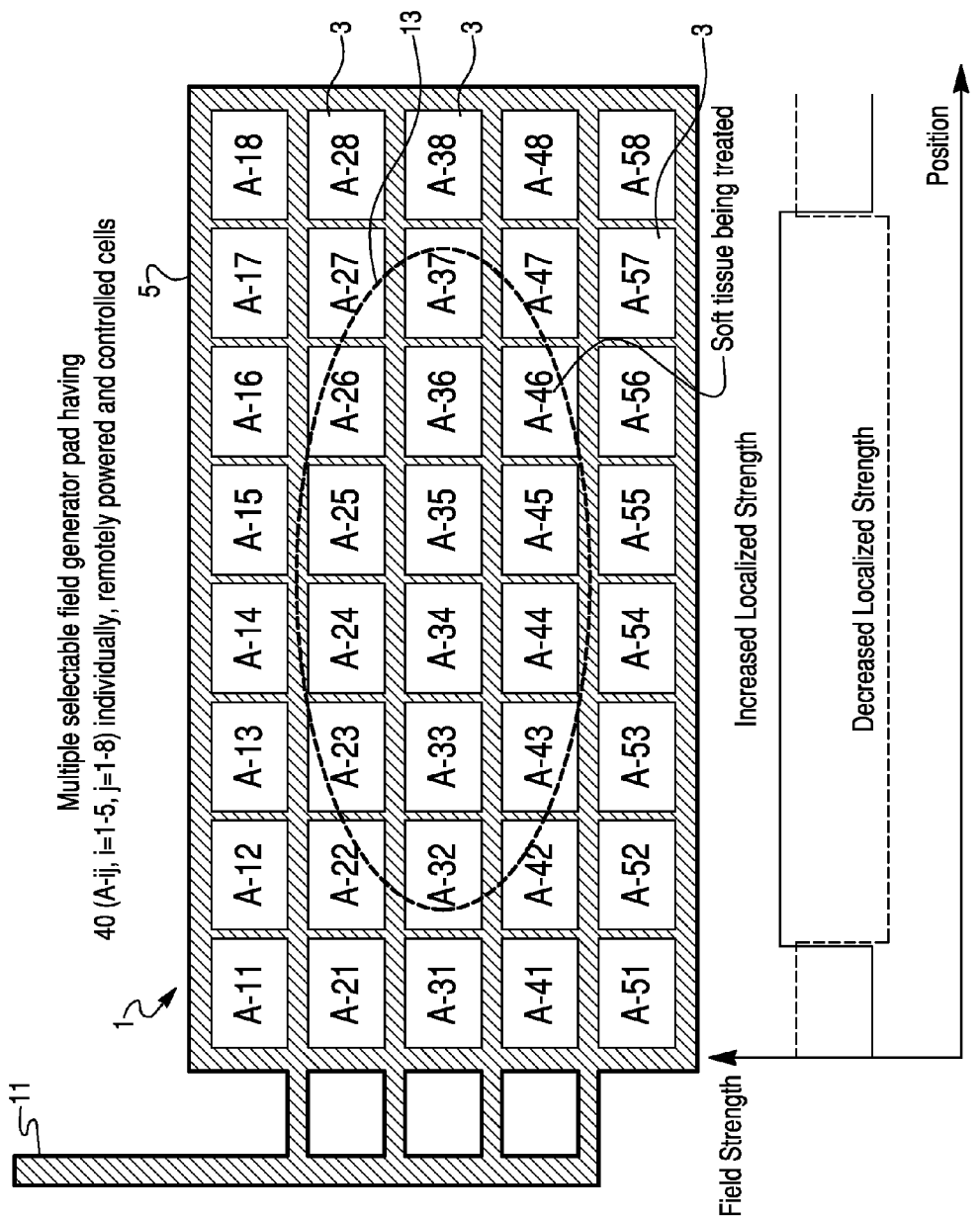
FIG. 6 is a diagram of a multiple selectable field generator pad having forty individual, remotely powered and controlled cells.
Figure 7:
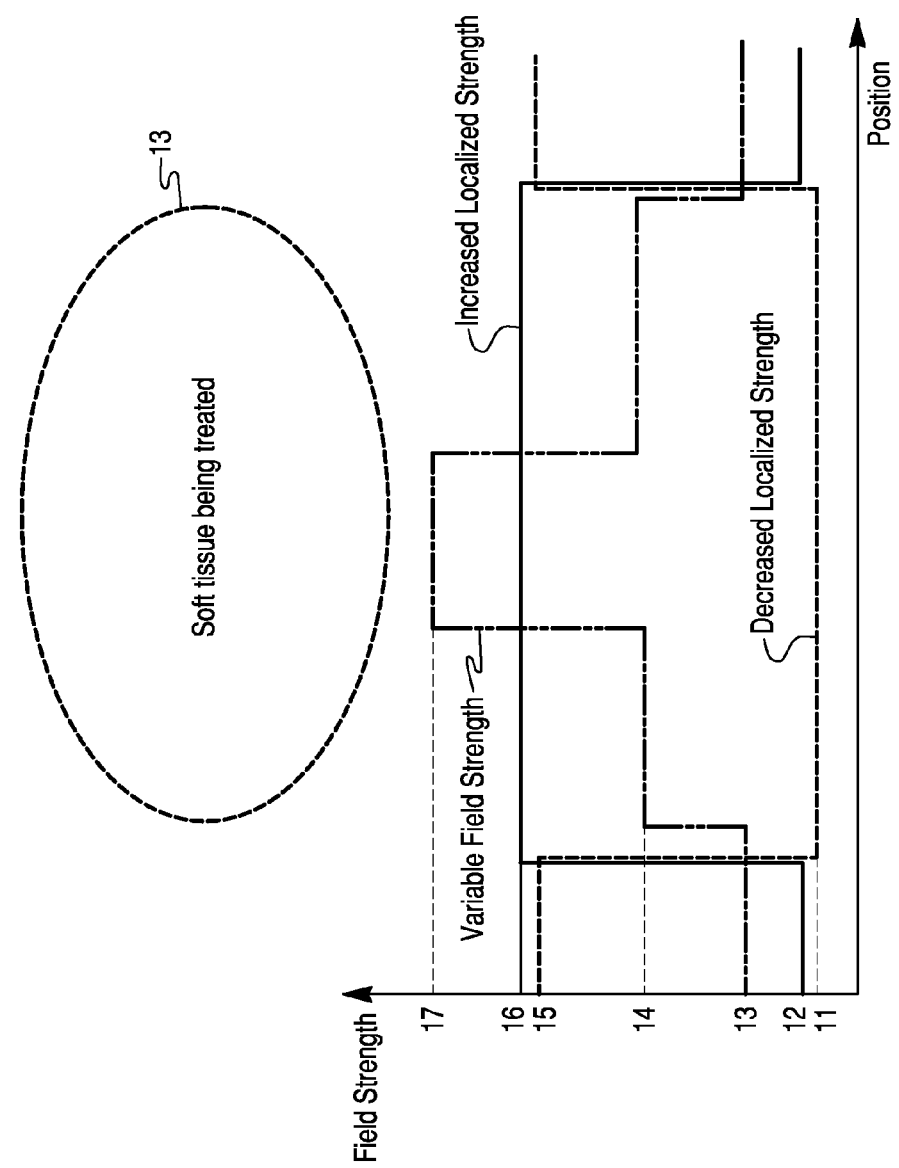
FIG. 7 is a plot of position against field strength in relation to the wounded area being treated.
Figure 8:
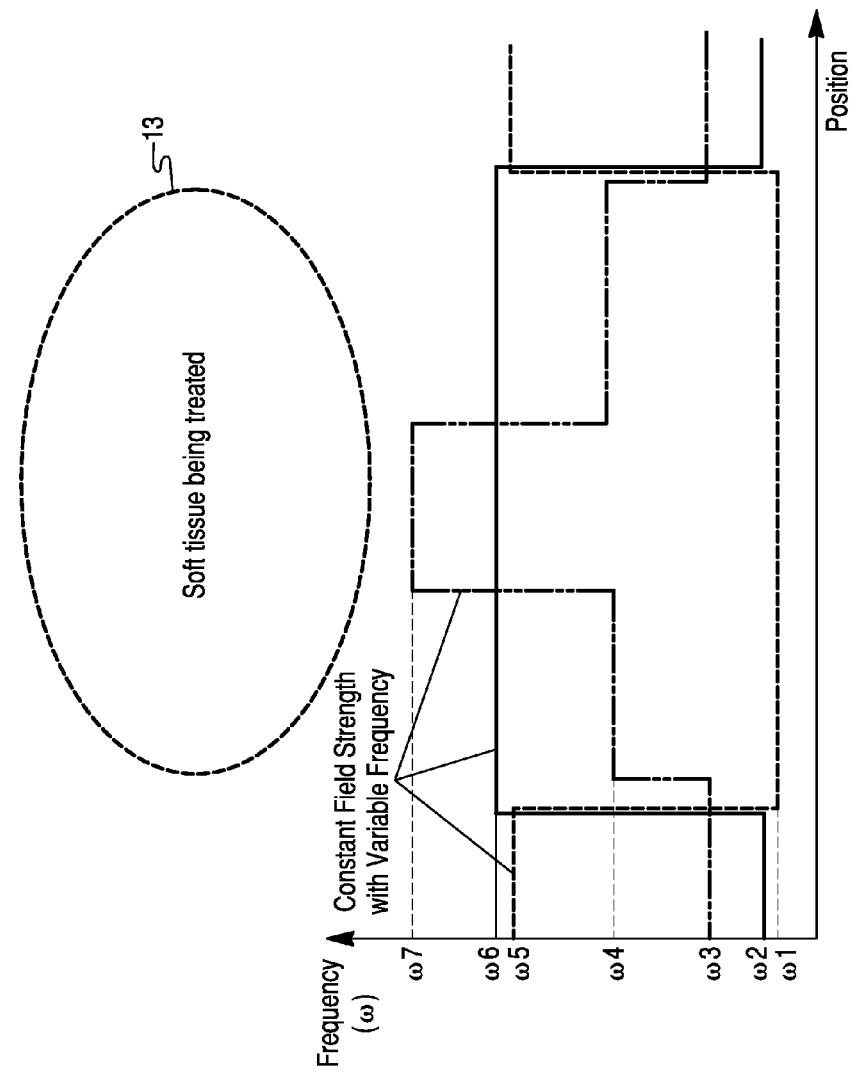
FIG. 8 is a plot of position against frequency in relation to the wounded area being treated.
Figure 9:
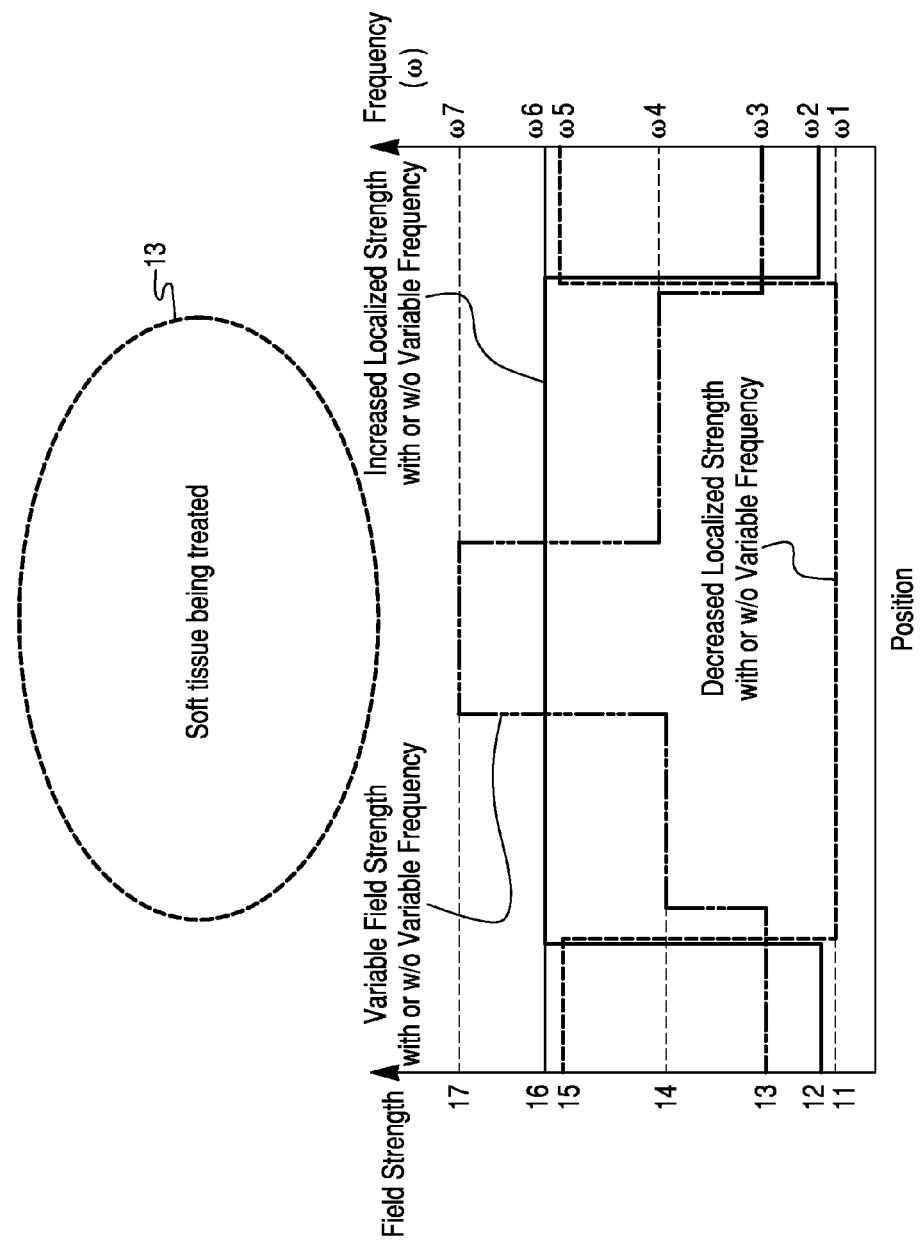
FIG. 9 is a plot of position against field strength and frequency in relation to the wounded area being treated.

FIG. 6 shows an example of how the pad 1 is placed over a wound 13 that is to be treated. FIGS. 7, 8 and 9 show the varying intensity of the individual cells in relation to the cell's proximity to the wound 13 that is to be treated.

Figure 10:
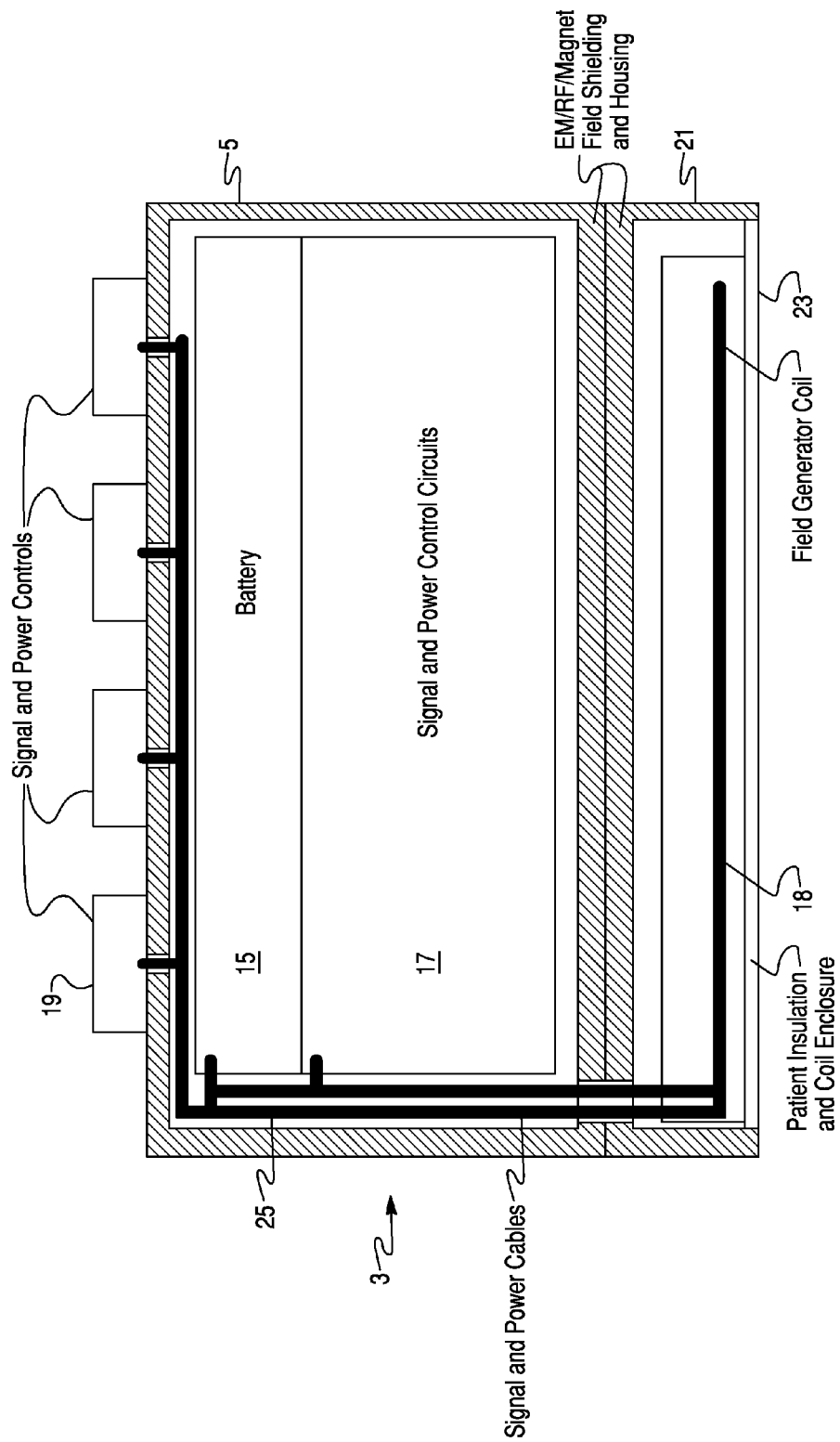
FIG. 10 is a block diagram of a self-contained EM/RF/magnet field unit cell.

FIGS. 10 and 11 show an individual cell 3 that contains controls within the cell itself. FIG. 10 shows a cell 3 that uses electromagnetic radiation, radio frequencies or a magnetic field to treat the wound. A battery 15 and signal and power control circuits 17 are both contained within the individual cell 3. Signals received by the signal and power controls 19 activate the battery 15 and the signal and power control circuits 17 that cause the field generator coil 18 to create a field. Signal and power cables 25 connect the signal and power controls 19, the battery 15, the signal and power control circuits 17, and the field generator coil 18 together. Shielding 21 around the cell 3 limits exposure to the generated field to only the wound that is to be treated. Insulation 23 houses the coil 18 and prevents direct contact with the coil by the patient.

FIG. 11 shows a cell 3 that uses current-voltage signals to treat the wound. A battery 15 and signal and power control circuits 17 are both contained within the individual cell 3, for internal control. However, the circuits may be outside the cell for generating and controlling current-voltage signals externally from a signal and control instrument or from a combined signal and control module. Some cells may have internal and some external generation and control as desired. The current-voltage cells may have one or more contacts with the body.

Signals received by the signal and power controls 19 activate the battery 15 and the signal and power control circuits 17 that cause the electrodes 27 to create an electrical signal. The electrodes 27 may be placed directly on the patient. Signal and power cables 25 connect the signal and power controls 17, the battery 15, the signal and power circuits 17, and the electrodes 27 together.

FIGS. 12 and 13 show an individual cell 3 that is remote controlled. FIG. 12 shows a cell 3 that uses electromagnetic radiation, radio frequencies or a magnetic field to treat the wound. Signal and power cables 25 connect the power supply to the individual cells 3. An on/off switch 31 located at each cell 3 supplies power to the field generator coil 18 for creating a field to treat the wound. The on/off switch 31 is used to select which individual cells 3 of the pad are to be used for treating the wound. Shielding 21 around the cell 3 limits exposure to the generated field to only the wound that is to be treated. Insulation 23 houses the coil 18 and prevents direct contact with the coil by the patient.

FIG. 13 shows a cell 3 that uses current-voltage signals to treat the wound. Signal and power cables 25 connect the power supply to the individual cells 3. An on/off switch 31 located at each cell 3 supplies power to the electrodes 27 for creating electrical signals to treat the wound. The on/off switch 31 is used to select which individual cells 3 of the pad are to be used for treating the wound. The electrodes 27 are placed directly on the patient.

Figure 14:
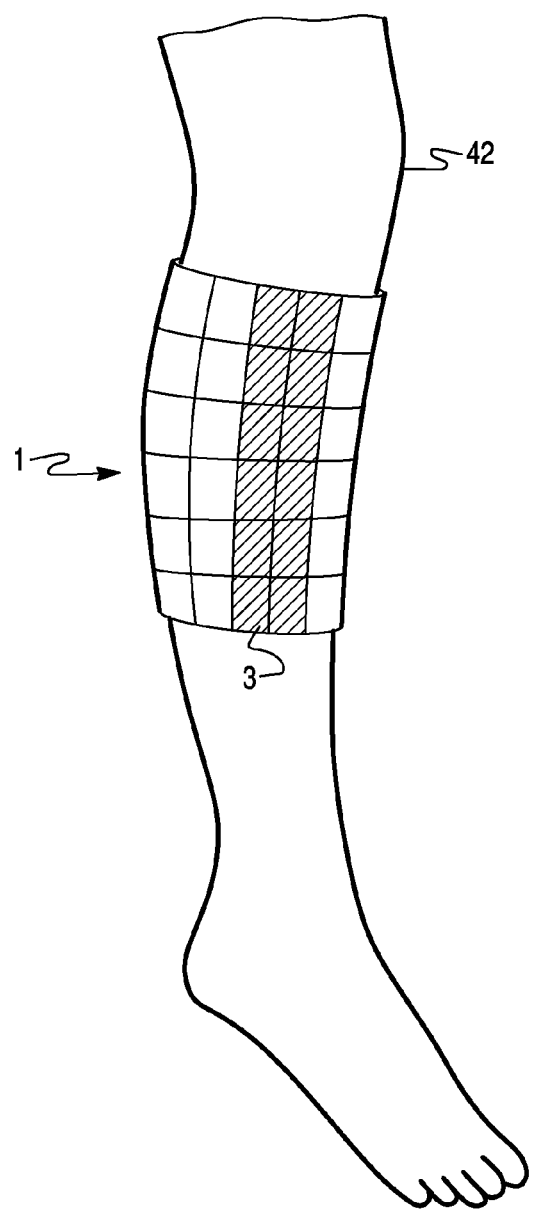
FIG. 14 is a diagram of a remote controlled/self-contained flexible, cylindrically shaped multiple unit cell for bone regrowth and other applications having any type activated region that has multiple RF/EM/B field/current-voltage control sensors.
Figure 15:
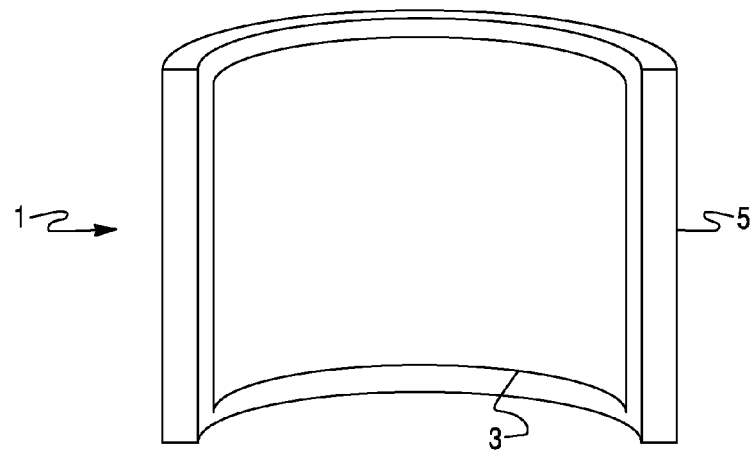
FIG. 15 is a diagram of a remote controlled/self-contained flexible, cylindrically shaped unit cell for bone regrowth and other applications.
Figure 16:
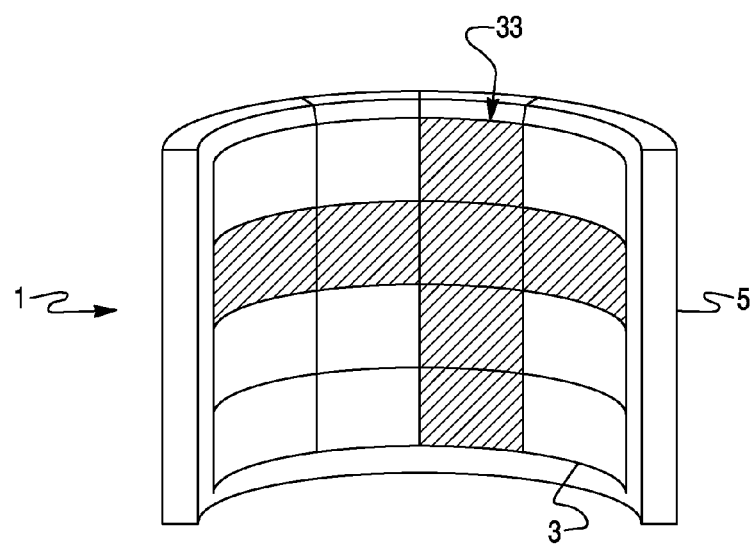
FIG. 16 is a diagram of a remote controlled, self-contained flexible, cylindrically shaped multiple unit cell for bone regrowth and other applications that has a cross type activated region.
Figure 17:
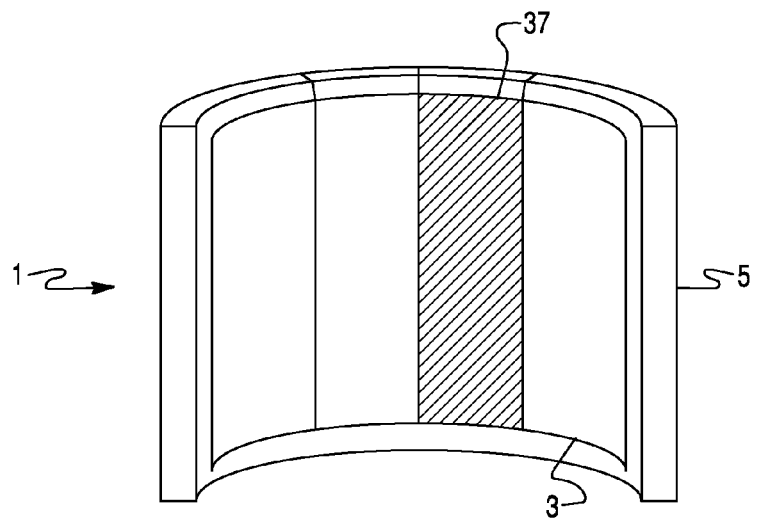
FIG. 17 is a remote controlled/self-contained flexible, cylindrically shaped multiple unit cell for bone regrowth and other applications having an elongated type activated region.
Figure 18:
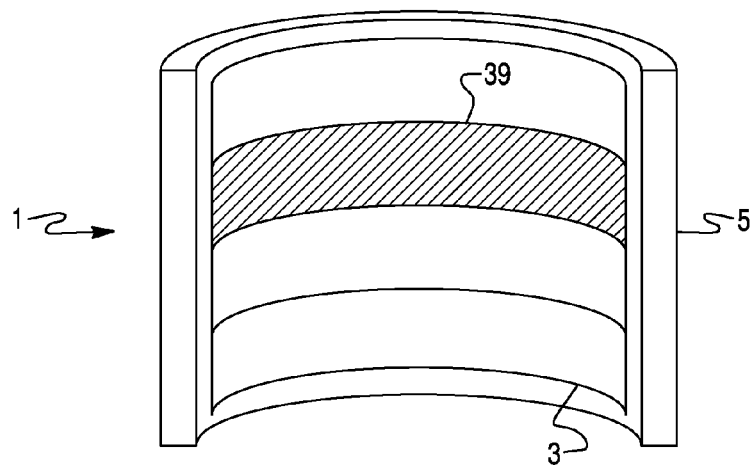
FIG. 18 is a remote controlled/self-contained flexible, cylindrically shaped multiple unit cell for bone regrowth and other applications that has a radial/helical type activated region.

The flexible nature of the pad 1 allows for shaping of the pad and applying it around a leg, arm or any other part of the body 42 that needs treatment, as shown in FIG. 14. The number of the activated cells as well as the shape of the area that is subjected to the RF/EM/B field or the current-voltage signals, or a combination thereof, and the signal strength, the frequency and other signal characteristics greatly depends on the shape and size of the wounded area to be treated. As shown in FIG. 15, the pad 1 may comprise one unitary cell 3, or the pad 1 may have multiple cells 3, as shown in FIG. 16. As shown in FIGS. 16, 17 and 18, the activated area may be cross 33, vertically 37 or horizontally 39 shaped. The cells may have varied shapes such as, but not limited to, quadrilateral, triangular, polygonal, orthogonal, circular or any other shape and combinations thereof. The size of individual cells are varied and are not limited to a particular size with combinations of sizes possible and within the scope of this invention.

Figure 19:
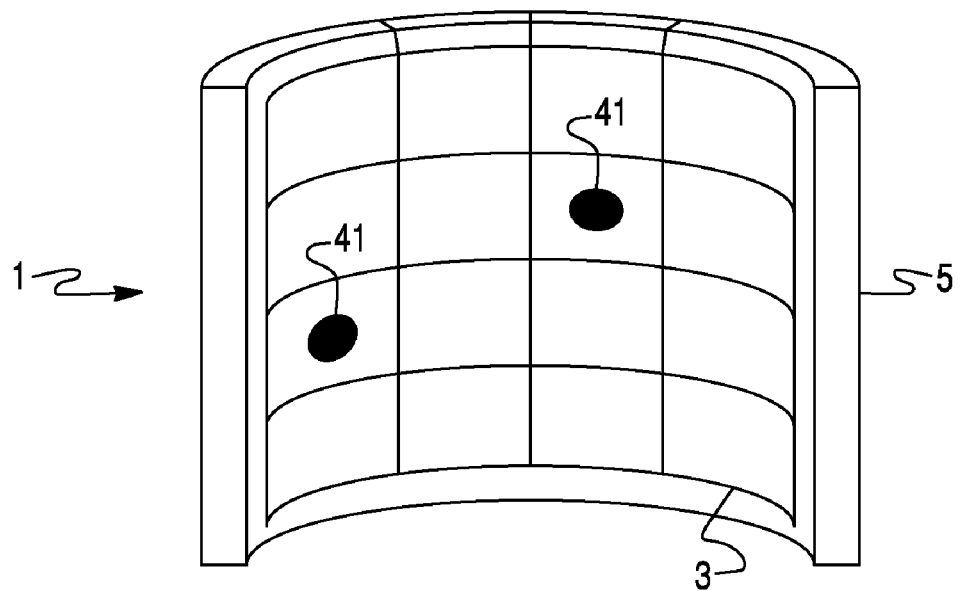
FIG. 19 is a remote controlled/self-contained flexible, cylindrically shaped multiple unit cell for bone regrowth and other applications having any type activated region having multiple RF/EM/B field/current-voltage control sensors.

Sensors 41 may be incorporated into the pad 1. The sensors may be used for measuring the dose of the treatment, the temperature of the treated area, blood pressure, or any other relevant parameters, as shown in FIG. 19.

The cost of maintenance of the pad and the effectiveness of the pad in treating patients is drastically lowered by simply repairing the defective pads.

While the invention has been described with reference to specific embodiments, modifications and variations of the invention may be constructed without departing from the scope of the invention, which is defined in the following claims.

I claim:

1. A healing cell apparatus comprising a base for placing on a body, a plurality of cells arranged on the base, a power supply individually communicating independently with each of the cells and controls connected to the cells separately controlling application of power to each of the cells individually, the power supply further comprising battery power supplies mounted on opposite ends of the base.

2. The apparatus of claim 1, wherein the base is thin, flexible and portable.

3. The apparatus of claim 1, wherein the cells generate energy selected from the group of energies consisting of radio frequencies, electro-magnetic radiations, magnetic fields, current-voltage signals, and combinations thereof.

4. The apparatus of claim 3 wherein frequency and field strength of the energies are variable with increasing frequencies in proximity to the wounds to be treated.

5. The apparatus of claim 1, wherein the controls further comprise self-contained controls in each cell.

6. The apparatus of claim 5, further comprising batteries connected to the self-contained controls.

7. The apparatus of claim 6, wherein the self-contained controls comprise control circuits connected to the batteries, cables connected to the control circuits, a field generator coil for generating energy connected to cables, a shielding separating the control circuits from the coil for shielding the control and any adjacent cells from interference, and a coil enclosure and patient insulation interposed between a patient and the coil.

8. The apparatus of claim 7, wherein the control circuits are power control circuits.

9. The apparatus of claim 7, wherein the control circuits are signal control circuits.

10. The apparatus of claim 7, wherein the cables are signal carrying cables.

11. The apparatus of claim 7, wherein the cables are power cables.

12. The apparatus of claim 7, wherein the energy is selected from a group of energies consisting of electro-magnetic radiations, radio frequencies, magnetic fields, and combinations thereof.

13. The apparatus of claim 7, wherein the battery, the control circuits, the shielding, the coil and the cables are surrounded by a housing.

14. The apparatus of claim 1, further comprising remote controls connected to the controls for controlling the cells remotely.

15. The apparatus of claim 14, wherein each cell further comprises cables, a field generator coil for generating energy, patient insulation interposed between a patient and the coil, a coil enclosure, and shielding for preventing interference.

16. The apparatus of claim 15, further comprising an on/off switch connected to the cables.

17. The apparatus of claim 15, wherein the cables are power cables.

18. The apparatus of claim 15, wherein the cables are signal carrying cables.

19. The apparatus of claim 15, wherein the energy is selected from a group of energies consisting of electro-magnetic radiations, radio frequencies, magnetic fields, and combinations thereof.

20. The apparatus of claim 14, wherein each cell further comprises cables connected to electrodes for producing current-voltage signals, patient insulation and a cable enclosure.

21. The apparatus of claim 20, wherein the cables are power cables.

22. The apparatus of claim 20, wherein the cables are signal carrying cables.

23. The apparatus of claim 20, further comprising an on/off switch connected to the cables.

24. The apparatus of claim 1, wherein the cells have an orthogonal arrangement on the base.

25. The apparatus of claim 1, further comprising control conduits mounted on the base.

26. The apparatus of claim 25, wherein the control conduits are connected to a power and signal generator and a generator a generator control.

27. The apparatus of claim 25, wherein the power and signal generator and generator control are portable.

28. The apparatus of claim 25, wherein the control conduits are power control conduits.

29. The apparatus of claim 25, wherein the control conduits are signal carrying control conduits.

30. The apparatus of claim 1, further comprising a control panel connected to the controls and mounted on one end of the base.

31. The apparatus of claim 1, further comprising control panels connected to the controls and mounted on opposite ends of the base.

32. The apparatus of claim 1, wherein the base encircles a limb on the body.

33. The apparatus of claim 1, further comprising sensors incorporated into the base.

34. A healing cell apparatus comprising a base for placing on a body, a plurality of cells arranged on the base, a power supply individually communicating independently with each of the cells and controls connected to the cells separately controlling application of power to each of the cells individually, the power supply further comprising a signal generator and control mounted on one end of the base, wherein the signal generator and control are mounted transverse from another signal generator and control on an opposite end of the base.

35. A healing cell apparatus comprising a base for placing on a body, a plurality of cells arranged on the base, a power supply individually communicating independently with each of the cells and controls connected to the cells separately controlling application of power to each of the cells individually, further comprising sensors incorporated into the base, wherein the sensors measure different parameters indicative of the wounds to be treated.

36. A healing cell apparatus comprising a base for placing on a body, a plurality of cells arranged on the base, a power supply individually communicating independently with each of the cells and controls connected to the cells separately controlling application of power to each of the cells individually, wherein the cells concurrently or sequentially generate radio frequencies, electromagnetic radiations, magnetic fields, current-voltage signals, and combinations thereof.

* * * * *